United States Patent [19]

Stern

[11] Patent Number: 4,556,713

[45] Date of Patent: Dec. 3, 1985

[54] 6-FLUORO-5-NITROQUINALDINE

[75] Inventor: Richard M. Stern, Cottage Grove, Minn.

[73] Assignee: Riker Laboratories, Inc., St. Paul, Minn.

[21] Appl. No.: 671,606

[22] Filed: Nov. 15, 1984

Related U.S. Application Data

[62] Division of Ser. No. 318,927, Nov. 6, 1981, Pat. No. 4,524,148.

[51] Int. Cl.[4] ............................................ C07D 215/18
[52] U.S. Cl. .................................... 546/180; 546/94; 546/165; 546/166; 546/171
[58] Field of Search ........................................ 546/180

[56] References Cited

FOREIGN PATENT DOCUMENTS

| 131632 | 9/1980 | Japan . |
| 27204 | 9/1980 | Japan . |
| 61776 | 11/1980 | Japan . |
| 59121 | 11/1980 | Japan . |
| 106776 | 12/1980 | Japan . |
| 131630 | 2/1981 | Japan . |
| 131631 | 5/1981 | Japan . |
| 135807 | 5/1981 | Japan . |
| 131629 | 5/1981 | Japan . |

OTHER PUBLICATIONS

Sveinbjornsson et al., J. Org. Chem., 16, (1951) pp. 1450–1452; C.A. 46: 5588d (1952).
Japan Kokai, 80-118416 9/11/80, C.A. 94: 71503t (1981).
March Adv. Org. Chem., McGraw Hill, NY, N.Y. 1968 pp. 313 and 554.
J. Mirek Chem. Abst., 62, 5252 (1965).
Jones (ed) "Heterocyclic Compounds" Quinolines, vol. 32, Wiley Inters. NY, N.Y. (1979) pp. 596–603.

*Primary Examiner*—Glennon H. Hollrah
*Assistant Examiner*—D. B. Springer
*Attorney, Agent, or Firm*—Donald M. Sell; James A. Smith; Carolyn A. Bates

[57] ABSTRACT

The compounds 8-bromo-6,7-dihydro-9-fluoro-5-methyl-1-oxo-1H,5H-benzo[ij]quiniolizine-2-carboxylic acid and 8-chloro-6,7-dihydro-9-fluoro-5-methyl-1-oxo-1H,5H,-benzo[ij]quinolizine-2-carboxylic acid are disclosed as potent antimicrobials. Pharmaceutically-acceptable carboxylate salts, acyl chlorides, esters and alkylaminoalkyl ester salts of the acids are also disclosed.

1 Claim, No Drawings

6-FLUORO-5-NITROQUINALDINE

This is a division of application Ser. No. 318,927 filed Nov. 6, 1981, now U.S. Pat. No. 4,524,148.

TECHNICAL FIELD

This invention relates to derivatives of the heterocyclic system known as benzo[ij]quinolizine. More specifically it relates to substituted 6,7-dihydro-5-methyl-1-oxo-1H,5H-benzo[ij]quinolizine-2-carboxylic acids and acyl chlorides, esters and salts thereof and the use of these compounds as antimicrobial agents. Intermediates for the preparation of the compounds and synthetic processes are also included within the scope of the invention.

BACKGROUND ART

Certain substituted 6,7-dihydro-1-oxo-1H,5H-benzo[ij]quinolizine-2-carboxylic acids are known to have antimicrobial activity and are disclosed in U.S. Pat. No. 3,896,131 (Gerster). Gerster discloses compounds substituted by halogen in the 8 or 9 position, but no compound substituted by halogen in both the 8 and 9 positions is described. It has now been found that certain compounds substituted by two different halogens in the 8 and 9 positions demonstrate greatly enhanced antimicrobial activity against certain key species of bacteria.

Specific compounds containing a halogen in the 8 or 9 position described by Gerster in the aforementioned patent include the 9-fluoro compound, the 8-chloro compound, the 9-chloro compound, the 10-chloro compound and the 9-bromo compound. Compounds substituted by halogen and one additional substituent in the 8 and 9 positions specifically disclosed by Gerster include: 8-chloro-9-methyl; 8-chloro-9-methoxy; 8-amino-9-chloro; and 8-acetamido-9-chloro. Compounds of the present invention exhibit greatly improved antimicrobial activity over the halogen-substituted compounds disclosed by Gerster.

DESCRIPTION OF THE INVENTION

This invention relates to the compounds 8-bromo-6,7-dihydro-9-fluoro-5-methyl-1-oxo-1H,5H-benzo[ij]-quinolizine-2-carboxylic acid; 8-chloro-6,7-dihydro-9-fluoro-5-methyl-1-oxo-1H,5H-benzo[ij]quinolizine-2-carboxylic acid; and acyl chlorides, pharmaceutically-acceptable carboxylate salts, esters, and alkylaminoalkyl ester salts thereof.

The carboxylic acid compounds of the invention may be represented by the following formula

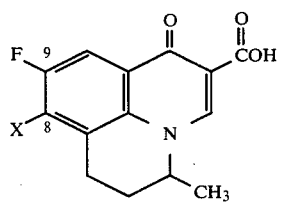

Formula (I)

wherein X is bromo or chloro. In the acyl halide derivatives, the hydroxyl portion of the carboxylic acid group is removed and replaced with a halide atom, preferably chlorine. In the ester derivatives, the hydrogen portion of the carboxylic acid group is replaced with an alkyl or substituted alkyl, preferably an alkylaminoalkyl group.

Esters and acyl chlorides of the compounds of the invention may be obtained as intermediates during the preparation of the acidic compounds, in some cases, or the esters may be prepared directly using standard synthetic methods. These esters and acyl chlorides exhibit antimicrobial activity, but they are primarily of interest as synthetic intermediates, although in some instances hydrolyzable or salt-forming esters may be of interest as therapeutic agents. Preferred esters are alkyl esters and alkylaminoalkyl esters having one to four carbon atoms in the alkyl group. Especially preferred are alkylaminoalkyl esters such as the dimethylaminoethyl esters which will form salts, e.g., hydrochlorides.

Ester derivatives are readily prepared by reacting the free acid of Formula I with thionyl chloride to provide the novel acyl chloride derivative. The acyl chloride is reacted with the appropriate alcohol to provide the desired ester.

It is well known to the art that pharmaceutically acceptable salts such as alkali metal, alkaline earth, aluminum, iron and other metal and amine salts of pharmaceutically active acids are the equivalents of the acids, and in some cases may even offer advantages in absorption, formulation and the like. Pharmaceutically-acceptable carboxylate salts of the free acid compounds of the invention are readily prepared by reaction of the acid with a base and evaporation to dryness. The base may be organic, e.g., sodium methoxide or an amine, or inorganic, e.g., sodium hydroxide. Alternatively, a carboxylate salt, e.g. the sodium salt, may be displaced by a second cation e.g. calcium or magnesium, when the salt of the second cation is more insoluble in a selected solvent such as water.

Compounds of the invention have an optically active carbon at the 5-position. All such optical isomers are included within the scope of the invention.

The antimicrobial activity of the compounds of the present invention can be demonstrated by the known, standard plate dilution method for bacterial susceptibility to antibiotics. The culture medium employed permits susceptibility testing of fastidious microorganisms towards antibiotics, sulfonamides and other chemotherapeutic agents. Tryptone soy agar (oxoid) of the following composition is the culture medium.

| | |
|---|---|
| Oxoid tryptone | 15 g. |
| Oxoid soy peptone | 5 g. |
| Sodium chloride | 5 g. |
| Oxoid agar-agar No. 3 | 15 g. |
| Water | 1 liter |

Using this test, the compounds of the invention have been found to have a broad spectrum of activity against gram-positive and gram-negative microorganisms.

The compounds of the invention are active against microorganisms either in the absence or presence of 10 percent horse serum.

The test procedure used to determine activity as employed in connection with the present invention provides information on the amount of a compound which gives complete inhibition, partial inhibition or no inhibition of microbial growth on the agar plates. In the tests, the selected compound is added to the agar medium to give concentrations of zero, one, ten and one hundred milligrams per liter. A series of plates with these concentrations is prepared. Ten percent horse serum is added to one series of such plates. Aliquots of broth culture of any of twelve species of microorganisms are innoculated onto the agar plates contaning the various compound concentrations. The plates are incubated at 37° C. in a 10 percent carbon dioxide atmosphere for 18 to 24 hours. The microbial growth on each plate is read visually, and minimal inhibitory concentrations are recorded. Some of the microorganisms which are used for this test are:

1. *Staphylococcus aureus*
2. *Bacillus subtilus*
3. *Escherichia coli*
4. *Pseudomonas aeruginosa*
5. *Streptoccus sp.\**
6. *Asperigillus niger*
7. *Candida albicans*
8. *Acinetobacter lwoffi*
9. *Acinetobacter anitratum*
10. *Klebsiella pneumoniae*
11. *Streptococcus fecaelis*
12. *Serratia mercescens*

*strains isolated from dental caries in rats or hamsters at the National Institute of Dental Health and grown in PFY or APT agar.

All of the compounds of the invention (including salts, esters and acyl halides) possess antimicrobial activity towards one or more of the above microorganisms. Of specific significance is their high level of activity against Pseudomonas aeruginosa, a particulary bothersome species associated with many topical infections.

Each of the compounds of the invention have also shown activity against one or more anaerobic bacteria, for example Bacteroides sp. and Clostridium welchii. All of the acid compounds of the invention have shown useful activity towards Erwinia amylovora, a gram-negative microorganism responsible for the plant disease known as fire blight.

It will be understood by those skilled in the art that the species used are representative indicator species, as it would be impractical to screen against all miroorganisms. It is well known in the art that broad spectrum activity can be predicted on the basis of activity shown against selected representative bacterial species of microorganisms.

All of the compounds of the invention are active when administered orally to animals. They are excreted in the urine, and are effective urinary tract antibacterials in mammals. It is also contemplated that they may be used in the treatment of pulmonary infection, soft tissue infection, burn infections and bacteremias.

All of the compounds of the invention are active against microorganisms in vitro or topically. In vitro activity is useful in itself, since antimicrobial agents may be used for disinfecting and sterilizing, e.g., medical and dental equipment, as components of disinfecting solutions.

The acute oral toxicity of the compounds of the invention is generally moderate to low compared with the effective oral dose, and they have an acceptable therapeutic ratio ($LD_{50}/ED_{50}$).

The acidic compounds of the invention are ordinarily white or yellowish crystalline or amorphous materials when purified. They are substantially insoluble in water, lower alcohols or hydrocarbons and are more soluble in halogenated solvents, N,N-dimethylformamide and the like. The esters are generally somewhat more soluble in organic solvents. The salts, especially the alkali metal salts, have appreciate solubility in water and lower alcohols.

The compounds of the invention may be formulated by incorporating them into conventional pharmaceutical vehicles, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of compound used to treat, for example, a microbial urinary infection by oral administration, will be an effective amount less than a toxic amount. The amount to be administered to control an infection will depend on the species, sex, weight, physical condition and many other factors, but this judgment is well within the skill of the medical art. Usually the amount will be less than 100 mg./kg. per dose. Conveniently this is administered in the form of conventional pharmaceutical preparations such as capsules, tablets, emulsions, solutions and the like. Excipients, fillers, coatings, etc. are generally employed with tablets or capsules, as is well known in the art.

It is known to the art that antimicrobial agents are used as growth promoters in various animal and bird species. Although not yet verified, it is inferred from the outstanding antimicrobial activity that the compounds of the invention can be used for this purpose also. The acid compounds of the invention may also be used for the control of microbial (e.g., Erwinia amylovora) infections of plants, e.g., by spraying or dusting formulations of these compounds on the affected area.

The compounds of the invention are prepared starting with the known compound 6-fluoroquinaldine.

6-Fluoroquinaldine is nitrated with fuming nitric and sulfuric acids in the presence of sodium nitrite catalyst to provide the novel compound 6-fluoro-5-nitroquinaldine.

The nitro group is reduced catalytically, for example in the presence of palladium on charcoal. If this reaction is carried out in the presence of acetic anhydride the product is the novel compound 5-acetamido-6-fluoroquinaldine. This intermediate is further reduced catalytically in the presence of platinum on charcoal to provide the novel compound 5-acetamido-6-fluorotetrahydroquinaldine.

The tetrahydroquinaldine intermediate is condensed with diethyl ethoxymethylenemalonate by heating without solvent at 100° to 200° C. (preferably 140° to 150° C. for two hours) for several hours. The resulting novel intermediate is the compound of the formula:

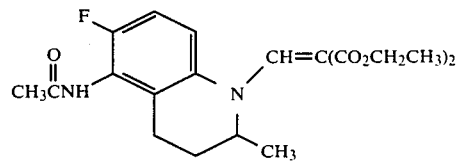

This novel intermediate is an oil which need not be isolated or purified. Instead, polyphosphoric acid is added, and the solution is heated at 100° to 140° C. to effect a condensation to provide an ester of the acids of Formula I wherein X is acetamido. The next step is saponification of the ester and hydrolysis of the acetamido group to provide 8-amino-6,7-dihydro-9-fluoro-5-methyl-1-oxo-1H,5H-benzo[ij]quinolizine-2-carboxylic acid, a novel intermediate. The 8-amino compound itself shows good antimicrobial activity against many species of microorganisms. This intermediate is converted to the 8-chloro or 8-bromo derivative by the Ullman modification of the Sandmeyer reaction in the presence of hydrochloric or hydrobromic acid, respectively.

The following examples are provided to illustrate the synthetic methods useful to obtain compounds of the invention, and are not intended to be limiting of the invention.

EXAMPLE 1

Part A. Preparation of the novel intermediate 6-Fluoro-5-nitroquinaldine

To 3.5 l of fuming sulfuric acid were added, with cooling, 600 g (3.73 moles) of 6-fluoroquinaldine in small portions (5 to 10 g). To this mixture was added about 0.1 g of sodium nitrite, followed by the dropwise addition of 261 ml of fuming red nitric acid over a period of six hours. The temperature of the mixture was maintained at 5° to 10° C. during the addition. The mixture was stirred at 20° C. for sixteen hours, then poured into 3 gallons of ice. Ammonium hydroxide was added, with cooling, to basify the mixture. The precipitated solid was separated by filtration, and dissolved in about two liters of warm toluene. The solution was dried over magnesium sulfate, filtered and evaporated to provide a yellow solid (6-fluoro-5-nitroquinaldine, m.p. 105°-108° C.) which was recrystallized from 1,2-dicholoroethane. The structural assignment was confirmed by nuclear magnetic resonance and infrared spectral analyses.

Part B. Preparation of the novel intermediate 5-Acetamido-6-fluoroquinaldine To a mixture of 20 g (0.1 mole) of 6-fluoro-5-nitroquinaldine in 180 ml of ethyl acetate and 20 ml of acetic anhydride were added 3 g of ten percent palladium on charcoal. The mixture was hydrogenated with hydrogen gas at 50 psi on a Paar apparatus for 20 minutes. The theoretical amount of hydrogen (25 psi) was used. On cooling, the mixture solidified to a yellow mass. About 200 ml of ethanol was added, and the mixture was heated to dissolve the product. The catalyst was filtered off through celite, and the filtrate was evaporated to dryness, leaving a yellow solid. This solid was triturated with 200 ml of water and neutralized with ten percent sodium hydroxide solution. Filtration and drying provided white crystals of 5-acetamido-6-fluoroquinaldine, m.p. 232°-235° C. The structural assignment was confirmed by infrared spectral analysis.

Part C. Preparation of the novel intermediate 5-Acetamido-6-fluorotetrahydroquinaldine In one liter of acetic acid were dissolved 95 g of 5-acetamido-6-fluoroquinaldine. To this mixture were added 10 g of five percent platinum on charcoal. The mixture was hydrogenated with hydrogen gas at 30 psi on a Paar apparatus for five hours. The amount of hydrogen used was 61 psi (verus 62 psi theoretical). The catalyst was removed by filtration, and the filtrate was concentrated to 250 ml and decanted into cold stirred sodium hydroxide solution. The white precipitate was separated by filtration and triturated with a chloroform/hexane (50/50) mixture to provide white crystals of 5-acetamido-6-fluorotetrahydroquinaldine, m.p. 168°-170° C. The structural assignment was confirmed by infrared spectral analysis.

Part D. Preparation of the novel intermediate Diethyl 2-[N-(5-Acetamido-6-fluorotetrahydroquinaldinyl)]methylenemalonate A stirred mixture of 6.4 g (28.8 mmole) of 5-acetamido-6-fluorotetrahydroquinaldine and 8 g (37 mmole) of diethyl ethoxymethylenemalonate was heated at 140°-150° C. for two hours. Ethanol was allowed to evolve. The product, diethyl 2-[N-(5-acetamido-6-fluorotetrahydroquinaldinyl)]methylenemalonate was not isolated.

Part E. Preparation of the novel intermediate 8-Amino-6,7-dihydro-9-fluoro-5-methyl-1-oxo-1H,5H-benzo[ij]quinolizine-2-carboxylic Acid The reaction mixture of part D containing diethyl 2-[N-(5-acetamido-6-fluorotetrahydroquinaldinyl)]methylenemalonate was treated with 25 g of polyphosphoric acid and warmed to 100° C. for 5 minutes while stirring. Foaming was observed, demonstrating that the reaction had commenced. The external heating was removed and stirring was continued for ten minutes. Heat was re-applied and the mixture was maintained at 100° C. for 0.5 hour. The cyclized product was then hydrolyzed (ester portion) and deacetylated (acetamido group) by adding 150 ml of water and 25 ml of methanol, basifying cautiously with fifty percent sodium hydroxide solution and heating at reflux for 2.5 hours. Filtration through decolorizing charcoal and celite and decantation into rapidly stirring dilute acetic acid provided a tan solid, hydrated 8-amino-6,7-dihydro-9-fluoro-5-methyl-1-oxo-1H,5H-benzo[ij]quinolizine-2-carboxylic acid, m.p. 300° C. Analysis: Calculated for $C_{14}H_{13}FN_2O_3 \cdot \frac{1}{2}H_2O$; %C,59.5; %H,4.8; %N, 9.9; Found: %C, 59.1; %H, 4.5; %N, 9.8

EXAMPLE 2

To 500 ml of 48 percent hydrobromic acid were added 14 g (50 mmole) of 8-amino-6,7-dihydro-9-fluoro-5-methyl-1-oxo-1H,5H-benzo[ij]quinolizine-2-carboxylic acid. The mixture was cooled to 5° C. with an ice-salt bath. To this stirred mixture 20 ml of 20 percent aqueous sodium nitrite solution were added dropwise over three minutes. Stirring was continued for ten minutes. To the solution were added 1.5 g of copper bronze. Stirring was continued for two hours at 20° C. The mixture was then heated on a steam bath for 30 minutes. The mixture was decanted into 1.25 l. of water. The tan solid was separated by filtration, then recrystallized from 200 ml of N,N-dimethylformamide. The product consisted of white crystals of 8-bromo-6,7-dihydro-9-fluoro-5-methyl-1-oxo-1H,5H-benzo[ij]quinolizine-2-carboxylic acid, m.p. 282°-285° C. Analysis: Calculated for $C_{14}H_{11}BrFNO_3$: %C, 49.4; %H, 3.3; %N, 4.1; Found: %C, 49.8; %H, 3.0; %N, 4.3. The structural assignment was confirmed by infrared and nuclear magnetic resonance spectral analyses.

EXAMPLE 3

A mixture of 15 ml of methanol and 15 ml of water containing 0.4 g (10 mmole) of sodium hydroxide was heated on a steam bath to dissolve 2.3 g (6.7 mmoles) of 8-bromo-6,7-dihydro-9-fluoro-5-methyl-1-oxo-1H,5H-benzo[ij]quinolizine-2-carboxylic acid. Cooling white stirring provided a cream-colored solid, hydrated sodium 8-bromo-6,7-dihydro-9-fluoro-5-methyl-1-oxo- 1H,5H-benzo[ij]quinolizine-2-carboxylate, m.p. 246° C. (dec.). Analysis: Calculated for $C_{14}H_{10}BrFNNaO_3 \cdot \frac{1}{3}H_2O$: %C, 45.7; %H, 2.9; %N, 3.8; Found: %C, 45.7;

compounds. The tests were run both in the absence and in the presence of horse serum as described hereinabove. The results are shown in the table below:

| COMPOUND | STREP. SPECIES | STAPHY. AUREUS | | ESCH. COLI | | PSEUDOMONAS AERUGINOSA | | ENTEROCOCCUS | | KLEBS. PNEUMONIA | |
|---|---|---|---|---|---|---|---|---|---|---|---|
| | | | | | | Minimum Inhibitory Concentration (mg/l) | | | | | |
| 9-Cl | 100 | 100 | 10 | 10 | 1 | 1 | I | I | NA | NA | NA | NA |
| 9-F | 100 | 100 | 10 | 10 | 1 | 1 | 100 | 100 | 100 | 100 | 1 | 1 |
| 9-Br | 100 | 100 | 100 | 100 | 10 | 10 | I | I | NA | NA | NA | NA |
| 8-Cl, 9-CH$_3$ | 100 | 100 | 10 | 100 | 10 | 10 | 100 | I | 100 | I | 100 | 100 |
| 8-Cl | 10 | 100 | 1 | 1 | 1 | 1 | 100 | 100 | 10 | 10 | 10 | 10 |
| 8-Cl, 9-OCH$_3$ | 100 | 100 | 10 | 10 | 10 | 10 | I | I | 100 | 100 | 100 | 100 |
| 8-NH$_2$, 9-Cl | I | I | 100 | 100 | 10 | 10 | I | I | 1 | 1 | 100 | 100 |
| 8-NHCOCH$_3$, 9-Cl | I | I | I | I | 10 | 10 | I | I | 1 | 1 | 100 | 100 |
| 8-Br, 9-F | 1 | 10 | .1 | .1 | .1 | .1 | 10 | 10 | 1 | 1 | 1 | 1 |
| 8-Br, 9-F sodium salt | 1 | 10 | .1 | .1 | .1 | .1 | 10 | 10 | 1 | 1 | 1 | 1P |
| 8-Cl, 9-F | 1P | 10 | .1 | .1P | .1 | .1 | 10 | 10 | 1 | 10 | 1 | 1 |
| 8-Cl, 9-F sodium salt | 1P | 10 | .1 | .1P | .1 | .1P | 10 | 10 | 1 | 1 | 1 | 1 |

I = Inactive
NA = Not Available

%H, 2.9, %N, 3.8. The structural assignment was confirmed by infrared and nuclear magnetic resonance spectral analyses.

EXAMPLE 4

In 100 ml of concentrated hydrochloric acid were dissolved 2.8 g (10 mmole) of 8-amino-6,7-dihydro-9-fluoro-5-methyl-1-oxo-1H,5H-benzo[ij]quinolizine-2-carboxylic acid. The mixture was cooled to 5° C. and 4 ml of 20 percent aqueous sodium nitrite solution was added dropwise with stirring. Stirring was continued at 5° C. for ten minutes. The ice bath was removed and 0.3 g of copper bronze was added. The mixture was stirred at 20° C. for two hours, then heated on a steam bath for ten minutes. The mixture was decanted into 250 ml of water. The tan solid precipitate was collected by filtration, then recrystallized from 40 ml of N,N-dimethylformamide. The product was a light tan solid, 8-chloro-6,7-dihydro-9-fluoro-5-methyl-1-oxo-1H,5H-benzo[ij]-quinolizine-2-carboxylic acid, m.p. 288°–291° C. Analysis: Calculated for $C_{14}H_{11}ClFNO_3$: %C, 56.9; %H, 3.8; %N, 4.7; Found: %C, 57.0; %H, 3.7; %N, 4.7. The structural assignment was confirmed by infrared and nuclear magnetic resonance spectral analyses.

EXAMPLE 5

To a mixture of 0.8 g (2.7 mmole) of 8-chloro-6,7-dihydro-9-fluoro-5-methyl-1-oxo-1H,5H-benzo[ij]-quinolizine-2-carboxylic acid and 20 ml of five percent sodium hydroxide solution were added 10 ml of methanol. The mixture was heated to obtain a solution, then cooled with stirring to provide a precipitate. The precipitate was washed with isopropanol, then with diethyl ether. The light tan solid was sodium 8-chloro-6,7-dihydro-9-fluoro-5-methyl-1-oxo-1H,5H-benzo[ij]quinolizine-2-carboxylate, m.p. 250° C. (dec.). Analysis: Calculated for $C_{14}H_{10}ClFNNaO_3$: %C, 52.9; %H, 3.2; %N, 4.4; Found: %C, 52.4; %H, 3.0; %N, 4.3. The structural assignment was confirmed by infrared spectral analysis.

EXAMPLE 6

The antibacterial activity of the compounds of the present invention and their sodium salts was compared to that of compounds described by Gerster in U.S. Pat. No. 3,896,131. Activity versus both gram negative and gram positive bacteria was much higher for the compounds of the present invention than any of the prior art compounds. The tests were run both in the absence and in the presence of horse serum as described hereinabove. The results are shown in the table below:

This test shows that the compounds of the invention are much better (up to 1000 times more active against some key species of bacteria) antibacterial agents than the compounds of the prior art. Against the best compound of the prior art, the 9-Fl compound, compounds of the present invention are more active in 9 of 12 tests and at least equal in the other 3 tests.

EXAMPLE 7

A mixture of 3.0 g of 8-bromo-6,7-dihydro-9-fluoro-5-methyl-1-oxo-1H,5H-benzo[ij]quinolizine-2-carboxylic acid, 25 ml of thionyl chloride and 2 drops of N,N-dimethylformamide was heated on a steam bath for 15 minutes. The excess thionyl chloride was removed by evaporation. The residue of solid 8-bromo-6,7-dihydro-9-fluoro-5-methyl-1-oxo-1H,5H-benzo[ij]quinolizine-2-carboxyl chloride was suspended in 100 ml of dichloromethane, the mixture was stirred and 10 ml of dimethylaminoethanol was added. After 10 minutes of stirring the solution was washed with sodium bicarbonate solution, then dried over magnesium sulfate. The solution was treated with decolorizing charcoal, filtered and concentrated to provide an oil. When cyclohexane was added, tan solid N,N-dimethylaminoethyl 8-bromo-6,7-dihydro-9-fluoro-5-methyl-1-oxo-1H,5H-benzo[ij]-quinolizine-2-carboxylate formed. This product was dissolved in 50 ml of hot isopropanol, treated with decolorizing charcoal and filtered. A solution of isopropanol saturated with hydrogen chloride gas was added until the mixture became acidic. The white precipitate that formed was N,N-dimethylaminoethyl 8-bromo-6,7-dihydro-9-fluoro-5-methyl-1-oxo-1H,5H-benzo[ij]-quinolizine-2-carboxylate hydrochloride, m.p. 250° C. (dec.) Analysis: Calculated for $C_{18}H_{20}BrFN_2O_3 \cdot HCl$: %C, 48.3; %H, 4.7; %N, 6.2; Found: %C, 48.4; %H, 5.0; %N, 6.2.

EXAMPLE 10

Solutions of 1.7 g sodium 8-bromo-6,7-dihydro-9-fluoro-5-methyl-1-oxo-1H,5H-benzo[ij]quinolizine-2-carboxylate in 40 ml warm water and 2 g calcium chloride in 20 ml warm water were stirred together, heated on a steam bath for 15 minutes and cooled about 16 hours. The product was separated by filtration, washed with water and dried to provide light pink calcium 8-bromo-6,7-dihydro-9-fluoro-5-methyl-1-oxo-1H,5H-benzo[ij]quinolizine-2-carboxylate hydrate, m.p. >300° C. Analysis: Calculated for $(C_{14}H_{10}BrFNO_3)_2Ca.\frac{1}{2}H_2O$: %C, 45.7; %H, 3.0; %N, 3.8; Found: %C, 45.7; %H, 3.2; %N, 3.8. The structural assignment was confirmed by infrared spectral analysis.

EXAMPLE 11

A solution of 1.0 g of sodium 8-bromo-6,7-dihydro-9-fluoro-5-methyl-1-oxo-1H,5H-benzo[ij]quinolizine-2-carboxylate in 30 ml of warm water was stirred with 1 g magnesium sulfate in 20 ml of water and warmed on a steam bath for 15 minutes. Cooling and filtration provided magnesium 8-bromo-6,7-dihydro-9-fluoro-5-methyl-1-oxo-1H,5H-benzo[ij]quinolizine-2-carboxylate hydrate, m.p. >300° C. Analysis: Calculated for $(C_{14}H_{10}BrFNO_3)_2Mg.H_2O$; %C, 47.1; %H, 3.0; %N, 3.9; Found: %C, 46.9; %H, 3.2; %N, 3.9.

What is claimed is:

1. The compound 6-fluoro-5-nitroquinaldine.

* * * * *